United States Patent
Hildebrand et al.

(10) Patent No.: US 6,752,517 B2
(45) Date of Patent: Jun. 22, 2004

(54) BATHTUB CHROMATHERAPY SYSTEM

(75) Inventors: Jeffrey C. Hildebrand, Sheboygan, WI (US); Carter J. Thomas, Cedarburg, WI (US); Anton J. Kolar, Sheboygan, WI (US)

(73) Assignee: Kohler Co., Kohler, WI (US)

( * ) Notice: Subject to any disclaimer, the term of this patent is extended or adjusted under 35 U.S.C. 154(b) by 0 days.

(21) Appl. No.: 10/068,395

(22) Filed: Feb. 6, 2002

(65) Prior Publication Data

US 2003/0147241 A1 Aug. 7, 2003

(51) Int. Cl.[7] .................................................. F21V 9/00
(52) U.S. Cl. ...................... 362/231; 362/230; 362/240; 362/241; 362/247; 362/800; 362/341; 362/343
(58) Field of Search .................. 210/169; 601/158; 239/20; 4/541.1–541.5, 546, 538, 584, 591; 362/101, 1, 2, 231, 800, 551, 560, 341, 343, 347, 349, 230, 241, 240, 247

(56) References Cited

U.S. PATENT DOCUMENTS

| 845,441 A | 2/1907 | Vaughan |
|---|---|---|
| 4,535,489 A | 8/1985 | Elkins |
| 4,587,600 A | 5/1986 | Morten |
| 4,887,197 A | 12/1989 | Effinger |
| 4,945,908 A | 8/1990 | Schneider |
| 4,992,704 A | 2/1991 | Stinson |
| 5,165,778 A | 11/1992 | Matthias et al. |
| 5,619,182 A | 4/1997 | Robb |
| 5,752,766 A | 5/1998 | Bailey et al. |
| 5,774,271 A * | 6/1998 | Lagerway et al. .......... 359/649 |
| 6,016,038 A | 1/2000 | Mueller et al. |
| 6,019,482 A | 2/2000 | Everett |
| 6,127,783 A * | 10/2000 | Pashley et al. ............. 315/149 |
| 6,149,283 A | 11/2000 | Conway et al. |
| 6,166,496 A | 12/2000 | Lys et al. |
| 6,200,002 B1 * | 3/2001 | Marshall et al. ............ 362/231 |
| 6,211,626 B1 | 4/2001 | Lyss et al. |
| 6,360,380 B1 * | 3/2002 | Swart et al. .................. 4/541.1 |

FOREIGN PATENT DOCUMENTS

| DE | 00103848 A2 * | 9/2000 | ............. A47K/3/02 |
|---|---|---|---|
| JP | 2001309865 A * | 11/2001 | ............. A47K/3/02 |
| WO | WO 02/36063 A2 * | 5/2002 | |

OTHER PUBLICATIONS

Drawings from U.S. application No. 08/633,400, filed Aug. 7, 2000, admitted prior art US 006360380 Pat Issued Mar. 26, 2002.

* cited by examiner

Primary Examiner—Sandra O'Shea
Assistant Examiner—A Tsidulko
(74) Attorney, Agent, or Firm—Quarles & Brady LLP

(57) ABSTRACT

A lighting system suitable for chromatherapy includes a plurality of light fixtures mounted through walls of a tub basin to project different color light into the water in the tub. The light fixtures are operated by a central control unit and each includes a housing having a concave internal surface. An array of light emitting diodes that project different color light is mounted under a cap covering one end of the housing. A lens is threaded onto the opposite end of the housing from within the tub basin to secure the light fixture to the tub. The concave surface has the different color light projected on it, and reflects light out the light fixture in mixed fashion.

10 Claims, 5 Drawing Sheets

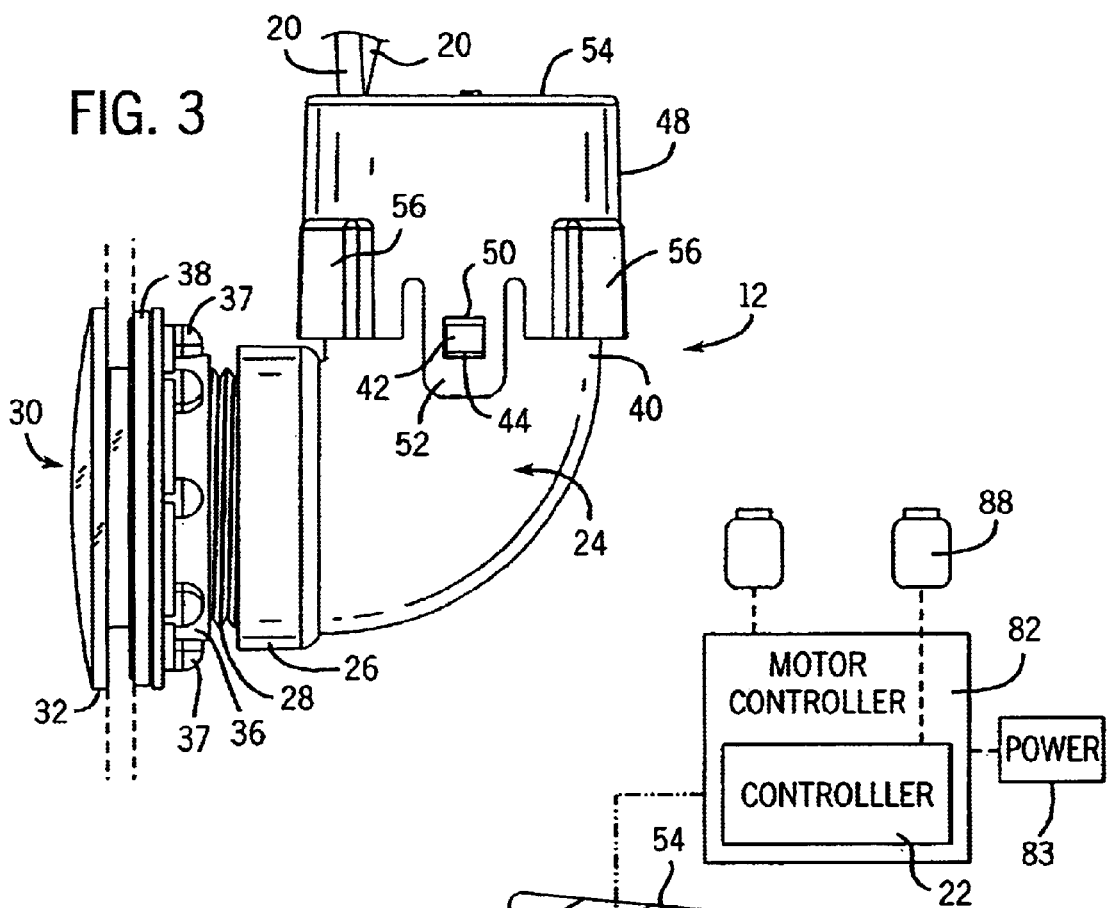
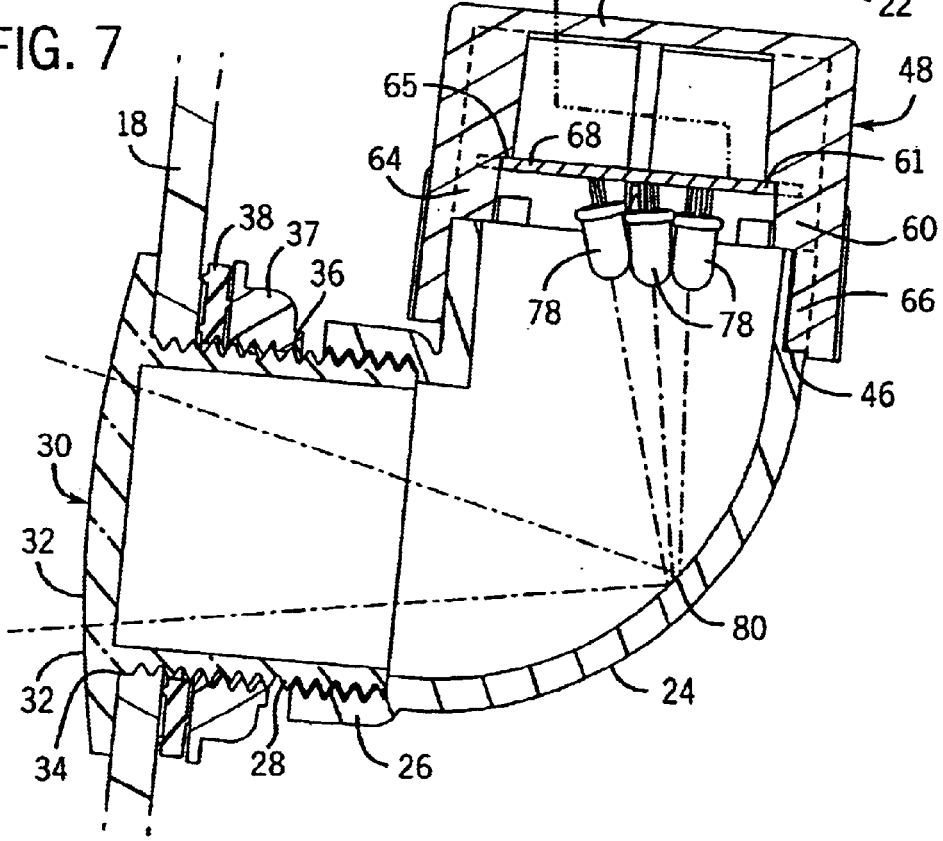

BATHTUB CHROMATHERAPY SYSTEM

CROSS-REFERENCE TO RELATED APPLICATION

Not applicable.

STATEMENT OF FEDERALLY SPONSORED RESEARCH OR DEVELOPMENT

Not applicable.

BACKGROUND OF THE INVENTION

The present invention relates to tubs such as bathtubs in which controllable lights are provided to illuminate the water with differing colors.

The presence or absence of light, and in particular colored light, is known to influence a person's mood at the time of the exposure. Over extended periods the presence or absence of such light may also have effects on physical, mental, spiritual and emotional well-being. In this regard, military personnel who are temporarily assigned to military bases near the Arctic Circle have shown marked increases in the incidence of depression during winters, absent exposure to artificial sources of light.

There are also those who believe that the differing frequencies of different colors may affect particular biological functions (e.g. the vibration of certain cells of the human body and thus certain biorhythmic functions) on more than a transitory basis. For example, some believe that when a human is exposed to prolonged red light that person's blood pressure will be higher even after the exposure, and the opposite will occur when the exposure is to a prolonged blue light.

Chromatherapy (the exposure of a human to colored light) has therefore been proposed for use to provide at least some relief for visual maladies, headaches, stress, anxiety, mental fatigue and depression. Some spas and holistic treatment centers even provide chromatherapy as a separate service or in conjunction with other treatments, such as facials, massage, acupuncture and treated baths.

Chromatherapy may be conducted in a room painted or illuminated with a particular color. However, another approach of increasing interest is to conduct chromatherapy by illuminating tub water with particular color or colors of light.

U.S. Pat. No. 885,441 discloses an early attempt at illuminating a pool with colored light, primarily for enhancing the aesthetic appearance of the pool. This early patent discloses a tank structure with slots beneath the floor in which were disposed ordinary incandescent lights mounted to removable slides located beneath glass windows in the floor of the tank. Another light was mounted over another window covered by a colored transparent film to illuminate the water with colored light. The inside surfaces of the tank were covered with luminous paint or other phosphorescent substance.

Small bathtubs have been devised having lighting systems for illuminating the bath water with particular color light. For example, U.S. Pat. No. 4,535,489 discloses a decorative bathtub with a transparent floor that was illuminated by white or colored light by a lamp mounted below the floor. U.S. Pat. No. 4,945,908 patent discloses a bath having multiple overhead and in-floor metal halide lamps emitting ultraviolet light rays.

A more recent bathtub chromatherapy system is disclosed in U.S. patent application Ser. No. 09/633,400, filed Aug. 7, 2000 and assigned to the assignee of the present invention. This application and the above mentioned patent are incorporated herein by reference as though fully set forth herein. The disclosed bathtub chromatherapy system uses a central incandescent light source and motorized color filter wheel to generate colored or white light directed to the end of a fiber optic bundle. Fiber optic cables carry the light to refractive lenses positioned at openings in the tub to illuminate the water. Desired colors can be selected and maintained or the colors can be automatically cycled.

While this system provides an enhanced chemotherapeutic bathing experience, it requires a rather complex motorized color wheel. Moreover, the incandescent bulb will eventually burn out and need to be replaced. This can be a problem if the tub is built into a tiled-in enclosure island with limited access to the tub bottom.

Thus, it can be seen that a need still exists for improved bathtub chromatherapy systems.

SUMMARY OF THE INVENTION

In one aspect the invention provides a lighting system for a tub containing a liquid. There is a first light emitting diode generating a first color light, a second light emitting diode generating a second color light, a control unit controlling the operation of the light emitting diodes, and a concave surface. The first and second light emitting diodes are positioned relative to the concave surface so as to be able to project the first and second color lights on the surface such that the surface reflects the lights in a mixed fashion.

In preferred forms the concave surface is on a surface of an inner bore of an elbow housing, the first and second light emitting diodes are positioned adjacent one end of the elbow housing, and a lens is positioned adjacent an opposite end of the housing. There can be even more such light emitting diodes, each of which projects light on the concave surface. In fact, there can be so many varied light colors that the mixed light can be white light when all are on, and alternatively at least one non-white light when less than all are on.

In other forms the light emitting diodes are positioned adjacent an inlet end of the elbow housing and the lens is attached to an outlet end of the elbow housing, and the inlet and outlet ends are perpendicular to each other. A cap is connectible to the elbow housing. The cap houses a circuit board to which the light emitting diodes are connected, and preferably also at least part of the light emitting diodes.

In another aspect there is also a tub with which the lighting system is used. The lens is mounted against an inner wall of the tub, and the elbow housing is mounted against an outer wall of the tub. In especially preferred forms there are a plurality of such elbow housings and lenses mounted through openings in the tub basin. For example, one unit can be mounted at the foot of the tub, and the other adjacent a back rest.

The system is particularly useful for chromatherapy applications such as in connection with a bathtub (e.g. especially a whirlpool). However, it may also be used for decorative purposes such as in connection with ornamental fountains.

The invention provides a compact light fixture operable by a control unit to selectively illuminate water in a tub with colored and/or white light. Because LEDs are used to generate the light, the light fixture is easy to maintain and requires little service. The concave reflecting surface provides an effective way of blending the colored light such that the resulting color at any given time is a single color, without striations.

Thus, depending on the desired effect, the water can be illuminated with soothing colors, such as pastels, or vibrant colors, such as primary colors. The light fixtures themselves are compact, light-weight and easily mountable to the tub walls without enlarging the overall dimensions of the tub.

These and other advantages of the invention will be apparent from the detailed description and drawings.

BRIEF DESCRIPTION OF THE DRAWINGS

FIG. 3 is a side view of a light fixture of the chromatherapy system;

FIG. 7 is a vertical sectional view of the FIG. 3 light fixture.

DETAILED DESCRIPTION OF THE PREFERRED EMBODIMENT

Figure 1:
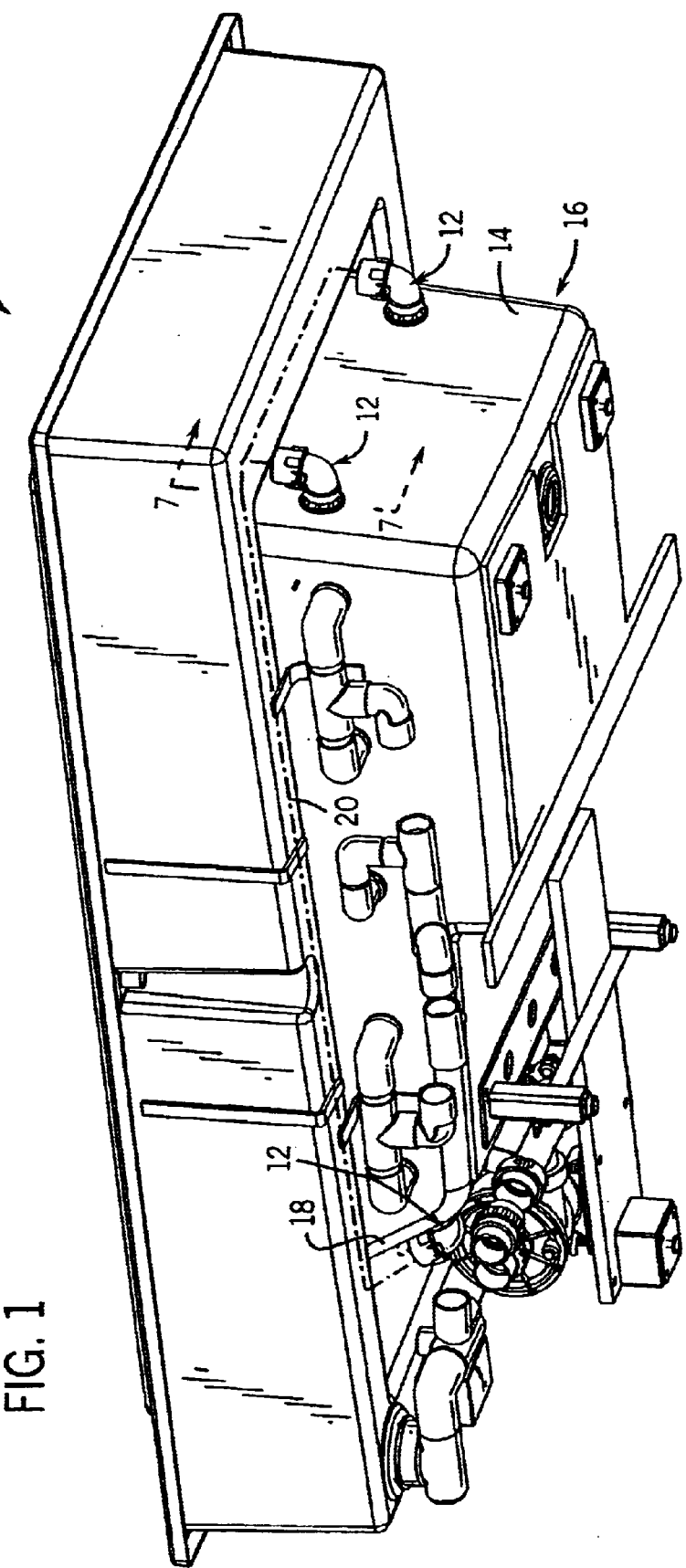
FIG. 1 is a bottom, right, frontal perspective view a bathtub having a chromatherapy system according to the present invention.
Figure 2:
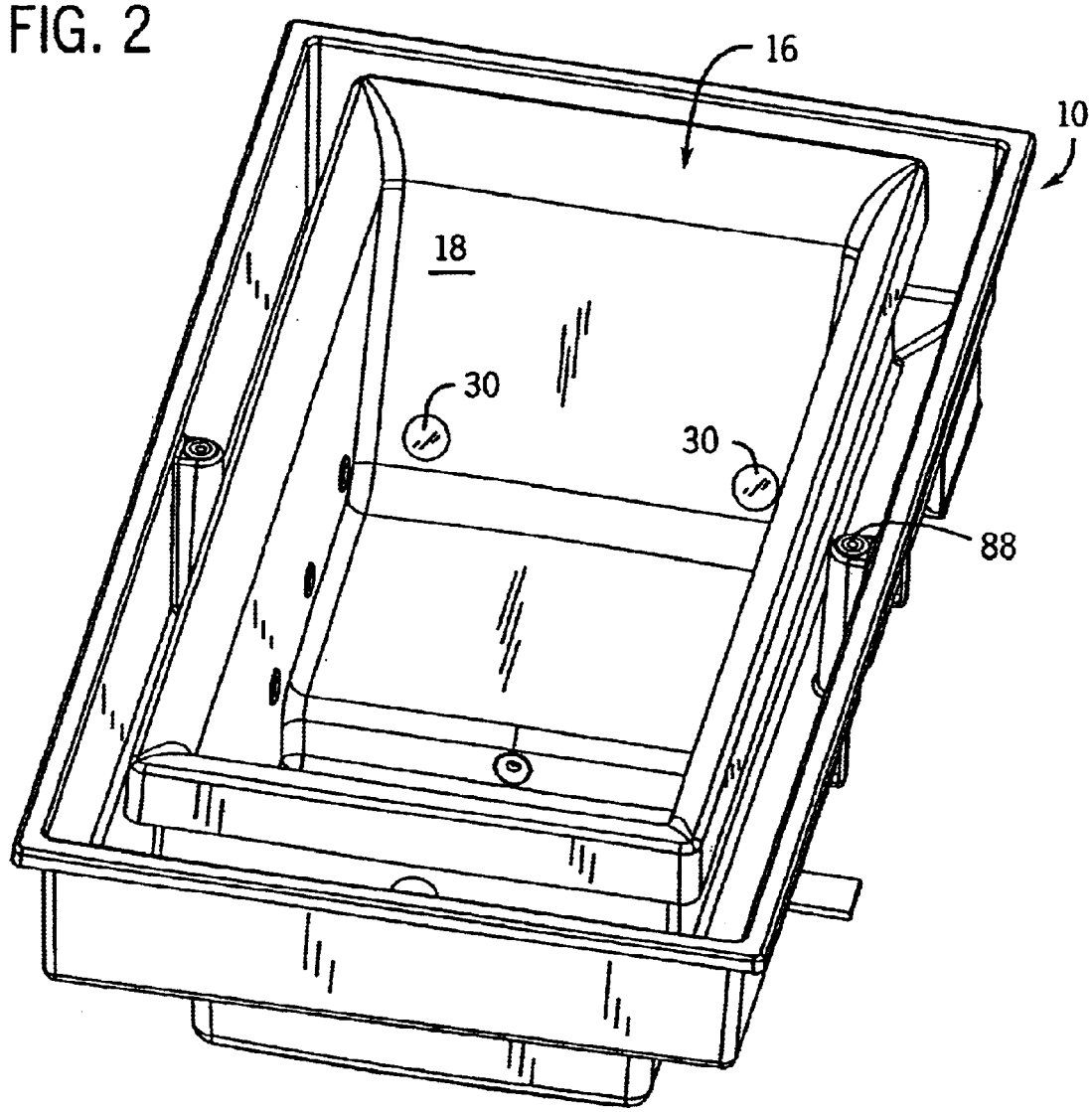
FIG. 2 is a left, upper, frontal perspective view thereof.

A preferred embodiment of the present invention is a bathtub with a chromatherapy system referred to generally by numeral 10. The bathtub shown in FIG. 1 is a whirlpool overflowing soaker tub of the type described in more detail in the aforementioned application incorporated by reference. However, the chromatherapy system of the present invention can work with a wide variety of tubs that contain water, regardless of whether used for bathing, and regardless of whether having whirlpool features. Examples could include whirlpool bathtubs, more conventional bathtubs, spa tubs, swimming pools, and pools around ornamental fountains.

In accordance with the preferred form of the invention, two light fixtures 12 are mounted through openings in a foot end wall 14 of the tub basin 16 and two such fixtures are mounted through openings in the back rest 18. Preferably, the openings are near the bottom of the tub basin.

The light fixtures 12 are electrically connected by wires 20 to a central controller unit 22 (see FIG. 7) that is preferably mounted to the underside of the tub. The control unit 22 has circuitry for controlling the operation of the light fixtures 12 as will be described below.

Figure 4:
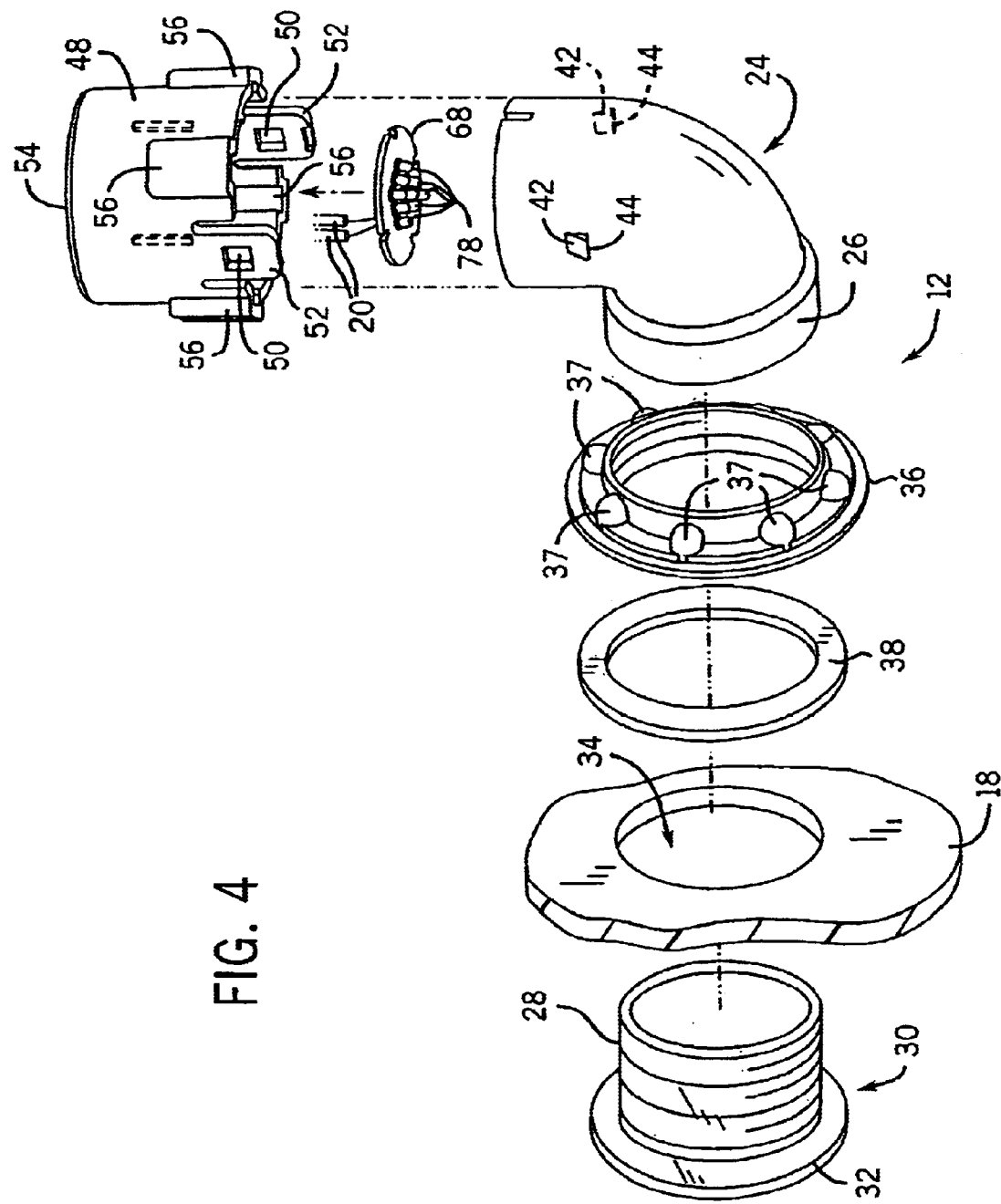
FIG. 4 is an exploded view of the light fixture of FIG. 3.

As will be best appreciated from FIGS. 3, 4 and 7, each light fixture 12 may be identical and includes an L-shaped tubular body or elbow 24, preferably a PVC pipe made of Cycolac® 5500 or 5600 ABS. A flared end 26 of the elbow 24 has internal threads that engage a cylindrical base end 28 of a refractive lens 30, preferably made of a translucent polycarbonate material. The lens 30 has a diffuser plate 32 with a diameter larger than the opening 34 in the tub basin 16 and abuts the inside of the tub when the cylindrical end 28 of the lens 30 is disposed in the opening 34. The lens 30 (and thus the light fixture 12) is secured to the tub basin 16 by a nut 36 (with grip features 37) that threads onto the cylindrical end 28 of the lens 30 and abuts the outside of the tub. A rubber gasket 38 is disposed between the tub and the nut 36 to create a water-tight seal at the opening 34.

The other end 40 of the elbow 24 has two catches 42 extending outwardly from opposite sides of the elbow 24. The catches 42 taper outwardly from the curved exterior surface of the elbow 24 to define a ledge 44 nearly perpendicular to the elbow 24. Between the two catches 42 is a locator recess 46 at the top edge of the elbow 24 opening outward.

The catches 42 allow a cap 48 to be snapped onto the elbow 24 by engaging square openings 50 in downwardly depending fingers 52. The tapered surfaces of the catches 42 ease the fingers 52 outward so that the openings 50 engage the ledges 44 to secure the cap 48 to the elbow 24. The cap 48 can be removed by prying the fingers 52 outward past the ledges 44, for example with a flat screw driver.

The cap 48 is preferably made of the same material as the elbow 24 and is generally cylindrical with a circular top wall 54. The cap 48 has four vents 56 projecting radially outward from the cylindrical wall so that air can pass into and out of the cap 48 when it is mounted on the elbow 24. The vents 56 open downwardly so that water cannot spill directly into the cap 48. The vents 56 allow air to circulate through the cap 48 and dry up any humidity or moisture present inside.

Figure 5:
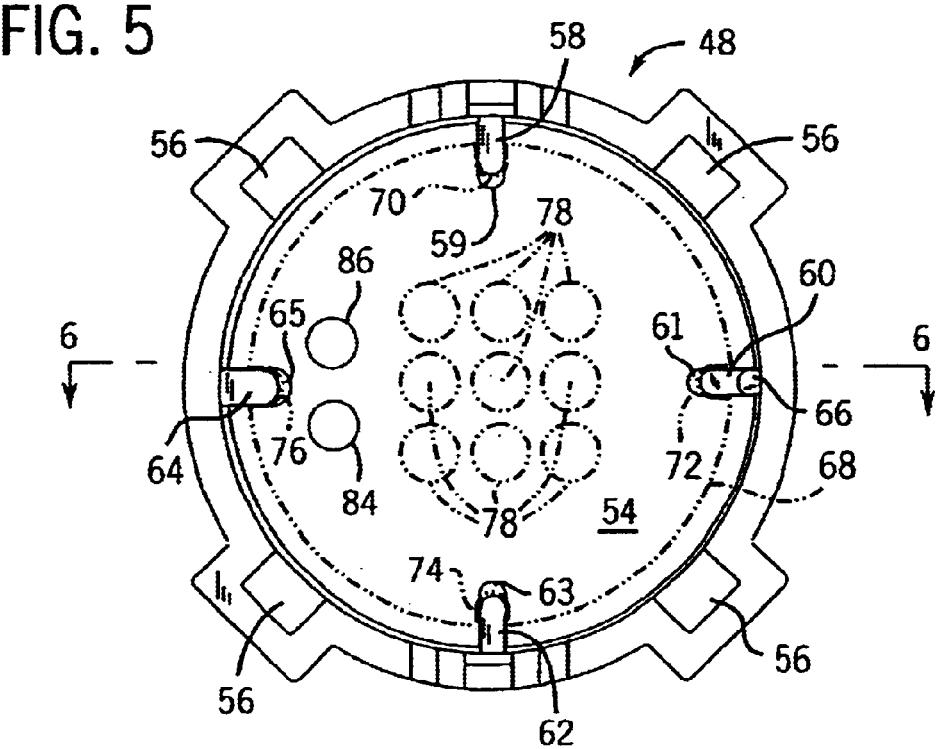
FIG. 5 is a bottom plan view of an upper part of the FIG. 3 light fixture.
Figure 6:
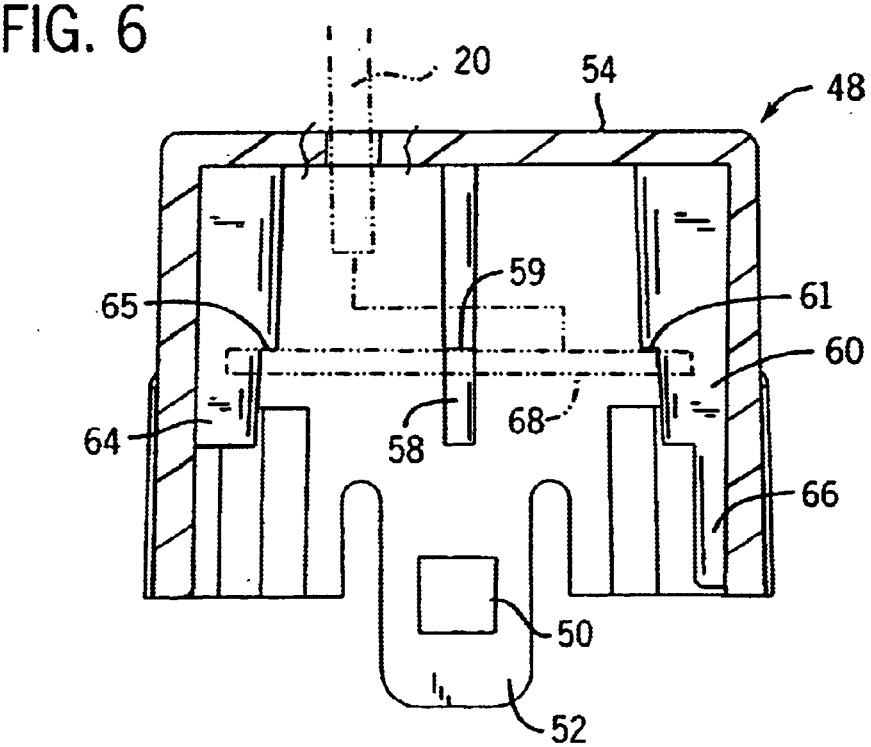
FIG. 6 is a sectional view taken along line 6—6 of FIG. 5.

As seen in FIGS. 5 and 6, the inside of the cap 48 has four vertical mounts spaced apart ninety degrees and extending in the direction of the centerline of the cap 48. Mounts 58, 60 and 62 are identical and define ledges 59, 61 and 63, respectively. Mount 64 is similar but thicker and defines ledge 65. A locator rib 66 is formed adjacent mount 60 and is sized to fit into the locator recess 46 of the elbow, and thereby fix the orientation of the cap 48 to the elbow 24.

The mounts 58, 60, 62 and 64 retain a circular circuit board 68 which has four notches 70, 72, 74 and 76 corresponding to the mounts. The circuit board 68 is secured to the ledges 59, 61, 63 and 65 with an epoxy and is maintained parallel to the top wall 54 of the cap 48.

As seen in FIG. 7, the circuit board 68 is linked to an array of light emitting diodes (LEDs) 78. Preferably, there are nine LEDs 78; three red, two blue, two green and two amber. The outer ring of LEDs 78 are mounted to the circuit board at an inward angle so that their individual light rays converge.

The position of the LEDs 78 and the orientation and position of the circuit board 68 is designed to direct the light rays of each LED to a region 80 at the inner surface of the elbow 24. More specifically, the region 80 is a concave surface at the bend in the elbow 24 that reflects light through the elbow 24 and the lens 30. Preferably, this region 80 is less than ½ inch. The entire inside surface of the elbow 24 has a SPE #1 finish and thus a high index of reflection.

Converging the light rays in this way allows them to mix before being reflected through the lens 80. This blends two or more different color light rays so that a single color is passed through the lens 30. Thus, individual light rays are not separately visible through the lens 30 (e.g. there are no shadows of odd colors). The net result is a single diffused color light even when different colored LEDs are illuminated simultaneously.

In the preferred embodiment, the nine LED array with four different colors (red, blue, green and amber) can produce eight distinct colors (lavender, blue, light blue, green, yellow, orange, red and white) depending on which LEDs are activated by the controller. It should be noted that other or additional colors could be generated with a chromatherapy system of the present invention by using a larger or different color combination LED array or by varying the intensity of one or more of the LEDs.

The control unit 22 includes a microprocessor that operates various transistors to turn on one or more of the LEDs 78 as needed to generate the desired color. For example, the green LEDs 78 are energized to produce green light and the red and blue LEDs 78 are energized to produce lavender light. All nine of the LEDs 78 are energized to produce white light.

In the disclosed embodiment, the control unit 22 is a peripheral to a motor controller 82 (see FIG. 1) operating the water jet system. It should be noted, however, that the control unit 22 could stand alone without the motor controller to provide a chromatherapy system for a conventional non-whirlpool bathtub.

Referring to FIG. 7, the control unit 22 is connected to the motor controller 82 and a power supply 83 in addition to the light fixtures 12. Preferably, the light fixtures 12 are connected together in a "daisy chain" with the wire from one light fixture connecting to the circuit board of the next light fixture through opening 84 in the top wall of its cap. Another wire then leads from the circuit board of this light fixture out opening 86 in the top of its cap to the next light fixture. Thus, only one cord runs into the control unit 22 from the light fixtures 12. In this arrangement, the LEDs of each light fixture 12 are energized the same so that the same color light is produced by all light fixtures 12.

The chromatherapy system can be activated and operated by a user sitting in the tub basin via a button 88, preferably a piezoelectric push button, at the deck surrounding the basin that is electrically coupled to the control unit 22 through the motor controller 82. The control unit 22 can be programmed so that the first time the button 88 is depressed all of the LEDs in each of the four light fixtures 12 will be energized, which produces a white light through each lens 30. The white light is sustained for approximately four seconds after which the controller sequences through each color, sustaining each for about eight seconds. When a desired color is illuminated, pressing the button 88 again will sustain the color indefinitely.

Pressing the button 88 again when the control unit 22 is out of the sequencing mode will shut off power to the light fixtures 12. Pressing the button 88 again will restore power to the light fixtures 12 which will illuminate the last sustained color.

The present invention thus provides a chromatherapy system for illuminating bath water with white or colored light to enhance the bathing experience. The light fixtures themselves are compact, light-weight and easily mountable to the tub walls. Since the light sources are generated from LEDs, they run much cooler than incandescent bulbs, and last much longer without replacement or service. The LED array can be constructed and controlled to emit a variety of colors without striations. All lights can be controlled while soaking in the tub by simply depressing one switch. Moreover, a system is provided to mix the lights, regardless of which light combination is chosen.

A preferred embodiment of the invention has been described in detail. However, the invention may be applied in a variety of other embodiments which are within the scope of the invention. For example, the system may only have red and blue LEDs. Thus, to ascertain the full scope of the invention, the following claims should be referenced.

INDUSTRIAL APPLICABILITY

The invention provides a chromatherapy system for bathtubs.

We claim:

1. A lighting system for a tub containing a liquid, the system comprising:
a first light emitting diode capable of generating a first color light;
a second light emitting diode capable of generating a second color light different from the first color light;
a control unit controlling the operation of the light emitting diodes; and
an elbow housing mounting the first and second light emitting diodes at one end and a lens at an opposite end with respect to the end with the first and second light emitting diodes, the housing having an internal concave surface a portion thereof defining a light mixing region receiving and mixing;
the first and second color lights before reflecting a third color light directly to the lens.

2. The lighting system of claim 1, wherein there are at least three such light emitting diodes, each of which projects light on the concave surface emits a different color light.

3. The lighting system of claim 2, wherein the lighting system can emit white light, and alternatively at least one non-white color light.

4. The lighting system of claim 1, wherein the light emitting diodes are positioned adjacent an inlet end of the elbow housing and the lens is attached to an outlet end of the elbow housing, and the inlet and outlet ends are perpendicular to each other.

5. The lighting system of claim 1, further comprising a cap connectible to the elbow housing.

6. The lighting system of claim 5, wherein the cap houses a circuit board to which the light emitting diodes are connected.

7. The lighting system of claim 1, further comprising a tub, wherein the lens is mounted against an inner wall of the tub, and the elbow housing is mounted against an outer wall of the tub.

8. The lighting system of claim 7, wherein there are a plurality of such elbow housings and lenses mounted to the tub.

9. The lighting system of claim 8, wherein the tub has a foot end wall and a back end wall, and at least one of such elbow housings is mounted adjacent the foot end wall, and at least one of the elbow housings is mounted adjacent the back end wall.

10. A lighting system for a tub containing a liquid, the system comprising:
a first light emitting diode capable of generating a first color light;
a second light emitting diode capable of generating a second color light different from the first color light;
a control unit controlling the operation of the light emitting diodes; and
an elbow housing having a lens at one end and at an opposite end an end cap mounting a circuit board electrically connecting the control unit to the first and second light emitting diodes, the housing having an internal concave surface a portion of which defines a light mixing region receiving and mixing the first and second color lights before passing through the lens.

* * * * *